United States Patent [19]
Sisti et al.

[11] Patent Number: 5,675,025
[45] Date of Patent: Oct. 7, 1997

[54] PACLITAXEL SYNTHESIS FROM PRECURSOR COMPOUNDS AND METHODS OF PRODUCING THE SAME

[75] Inventors: Nicholas J. Sisti, Jeffersonville; Charles S. Swindell, Merion; Madhavi C. Chander, Rosemont, all of Pa.

[73] Assignee: NaPro BioTherapeutics, Inc., Boulder, Colo.

[21] Appl. No.: 483,084

[22] Filed: Jun. 7, 1995

[51] Int. Cl.$^6$ .................................................. C07D 305/14
[52] U.S. Cl. ........................................... 549/510; 549/511
[58] Field of Search ........................................ 549/510, 511

[56] References Cited

U.S. PATENT DOCUMENTS

| | | | |
|---|---|---|---|
| 4,857,653 | 8/1989 | Colin et al. | 549/511 |
| 4,924,011 | 5/1990 | Denis et al. | 549/510 |
| 4,924,012 | 5/1990 | Colin et al. | 549/510 |
| 5,015,744 | 5/1991 | Holton | 549/510 |
| 5,136,060 | 8/1992 | Holton | 549/510 |

FOREIGN PATENT DOCUMENTS

| | | |
|---|---|---|
| 0400971A2 | 12/1990 | European Pat. Off. . |
| 0528729A1 | 2/1993 | European Pat. Off. . |
| 2687150A1 | 8/1993 | France . |
| WO91/13066 | 9/1991 | WIPO . |

OTHER PUBLICATIONS

"New and Efficient Approaches tothe Semisynthesis of Taxol and its C–13 Side Chain Analogs by Means of Beta–Lactam Synthon Method", Ojima et al, *Tetrahedron*, vol. 48, No. 34, pp. 6985–7012, 1992.

"Improved Protection and Esterification of a Precursor of the Taxotere and Taxol Side chains", Commereon et al., *Tetrahedron*, vol. 33, No. 36, pp. 5185–5188, 1992.

"Highly Stereocontrolled and Efficient Preparation of the Protected Esterificatoin–Ready Docetaxel (Taxotere) Side Chain", Kanazawa et al, *J. Org. Chem.*, vol. 59, No. 6, pp. 1238–1240, 1994.

*Primary Examiner*—Ba K. Trinh
*Attorney, Agent, or Firm*—Timothy J. Martin; Michael R. Henson

[57] ABSTRACT

An efficient protocol for the synthesis of taxol, taxol analogs and their intermediates is described. The process includes the attachment of the taxol A-ring side chain to baccatin III and for the synthesis of taxol and taxol analogs with variable A-ring side chain structures. A rapid and highly efficient esterification of O-protected isoserine and 3-phenylisoserine acids having N-benzyoloxycarbonyl groups to the C-13 hydroxyl of 7-O-protected baccatin III is followed by a deprotection-acylation sequence to make taxol, celphalomanninne and various analogs, including photoaffinity labeling candidates.

8 Claims, No Drawings

PACLITAXEL SYNTHESIS FROM PRECURSOR COMPOUNDS AND METHODS OF PRODUCING THE SAME

FIELD OF THE INVENTION

This invention generally relates to the synthesis of paclitaxel from precursor compounds. More particularly, though, this invention concerns the semi-synthesis of taxol using a protected baccatin III backbone which is esterified with a suitably protected side chain acid to produce an intermediate that may thereafter be acylated and deprotected to produce paclitaxel.

BACKGROUND OF THE INVENTION

The chemical compound referred to in the literature as taxol, and more recently "paclitaxel", has received increasing attention in the scientific and medical community due to its demonstration of anti-tumor activity. Paclitaxel has been approved for the chemotherapeutic treatment of several different varieties of tumors, and the clinical trials indicate that paclitaxel promises a broad range of potent anti-leukemic and tumor-inhibiting activity. As is known, paclitaxel is a naturally occurring taxane diterpenoid having the formula and numbering system as follows:

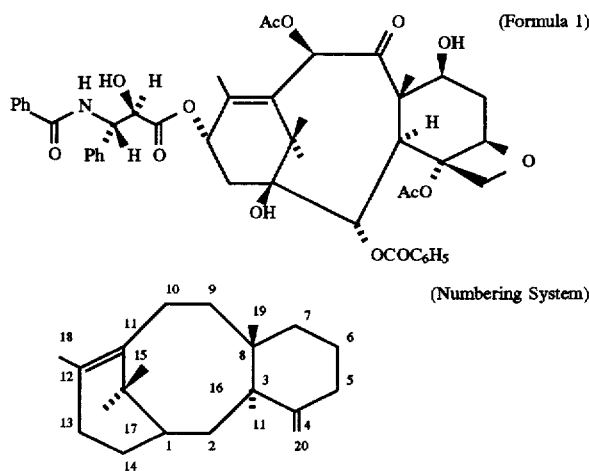

(Formula 1)

(Numbering System)

While the paclitaxel molecule is found in several species of yew (genus Taxus, family Taxaceae), the concentration of this compound is very low. Moreover, these evergreens are slow-growing. Thus, a danger exists that the increasing use of paclitaxel as an effective anti-cancer agent will deplete natural resources in the form of the yew trees. Indeed, while the bark of the yew trees typically exhibit the highest concentration of paclitaxel, the production of 1 kilogram of paclitaxel requires approximately 16,000 pounds of bark. Thus, the long term prospects for the availability of paclitaxel through isolation is discouraging.

The paclitaxel compound, of course, is built upon the baccatin III backbone, and there are a variety of other taxane compounds, such as baccatin III, cephalomanine, 10-deacetylbaccatin III, etc., some which are more readily extracted in higher yields from the yew tree. Indeed, a relatively high concentration of 10-deacetylbaccatin III can be extracted from the leaves of the yew as a renewable resource. Typically, however, these other taxane compounds present in the yew tree do not exhibit the degree of anti-tumor activity shown by the paclitaxel compound.

Since the paclitaxel compound appears so promising as a chemotherapeutic agent, organic chemists have spent substantial time and resources in attempting to synthesize the paclitaxel molecule. A more promising route to the creation of significant quantities of the paclitaxel, compound has been proposed by the semi-synthesis of paclitaxel by the attachment of the A-ring side chain to the C-13 position of the naturally occurring baccatin III backbone derived from the various taxanes present in the yew. See, Denis et al, a "Highly Efficient, Practical Approach to Natural Taxol", *Journal of the American Chemical Society*, page 5917 (1988). In this article, the partial synthesis of paclitaxel from 10-deacetylbaccatin III is described.

The most straightforward implementation of partial synthesis of paclitaxel requires convenient access to chiral, non-racemic side chain and derivatives, an abundant natural source of baccatin III or closely related diterpenoid substances, and an effective means of joining the two. Of particular interest then is the condensation of baccatin III or 10-deacetylbaccatin III with the paclitaxel A-ring side chain. However, the esterification of these two units is difficult because of the hindered C-13 hydroxyl of baccatin III located within the concave region of the hemispherical taxane skeleton. For example, Greene and Gueritte-Voegelein reported only a 50% conversion after 100 hours in one partial synthesis of paclitaxel. *J. Am. Chem. Soc.*, 1988, 110, 5917.

In U.S. Pat. No. 4,929,011 issued May 8, 1990 to Denis et al entitled "Process for Preparing Taxol", the semi-synthesis of paclitaxel from the condensation of a (2R,3S) side chain acid of the general formula:

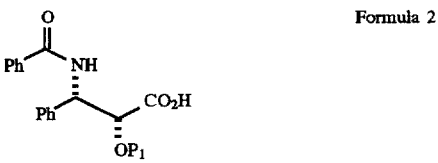

Formula 2 wherein $P_1$ is a hydroxy protecting group with a taxane derivative of the general formula of:

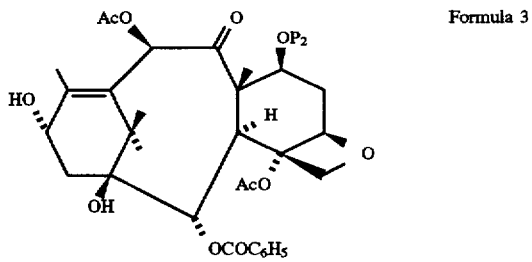

Formula 3 wherein $P_2$ is a hydroxy protecting group is described wherein the condensation product is subsequently processed to remove the $P_1$ and $P_2$ protecting groups. In Denis et al, the (2R, 3S) 3-phenylisoserine derivative, with the exception of the $P_1$ protecting group, is the A-ring side chain for the paclitaxel molecule. The $P_2$ protecting group on the baccatin III backbone is protected by, for example, a trimethylsilyl or a trialkylsilyl radical.

An alternative semi-synthesis of paclitaxel is described in co-pending U.S. patent application Ser. No. 08/357,507 to Swindell et al. This application discloses semi-synthesis of paclitaxel from a baccatin III backbone by the condensation with a side chain having the general formula:

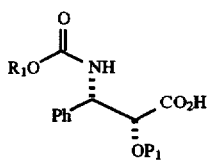

Formula 4 wherein $R_1$ is alkyl, olefinic or aromatic or $PhCH_2$ and $P_1$ is a hydroxyl protecting group The side chain in Swindell et al is distinct from the side chain attachment used in Denis et al, above, in that the nitrogen is protected as a carbamate. Preferably, the A-ring side chain is benzyloxycarbonyl (CBZ) protected. After esterification, the CBZ protecting group is removed and replaced by PhCO to lead to paclitaxel. This process generated higher yields than that described in Denis et al. In Swindell et al, Ser. No. 08/357,507, the preferred masking groups were selected to be trichloroethoxymethyl or trichloroethoxycarbonyl. Benzyloxymethyl (BOM) was, however, disclosed as a possible side chain hydroxl protecting group for the 3-phenylisoserine side chain, but, according to the processes described therein, the BOM protecting group could not be removed from the more encumbered C-2' hydroxyl in the attached 3-phenylisoserine side chain. The use of the BOM protected side chain was not extensively investigated, for this reason.

U.S. Pat. No. 4,924,012, issued May 8, 1990 to Colin et al discloses a process for preparing derivatives of baccatin III and of 10-deacetylbaccatin III, by condensation of an acid with a derivative of a baccatin III or of 10-deacetylbaccatin III, with the subsequent removal of protecting groups by hydrogen. Several syntheses of TAXO-TERE® (Registered to Rhone-Poulenc Sante) and related compounds have been reported in the *Journal of Organic Chemistry*: 1986, 51, 46; 1990, 55, 1957; 1991, 56, 1681; 1991, 56, 6939; 1992, 57, 4320; 1992, 57, 6387; and 993, 58, 255; also, U.S. Pat. No. 5,015,744 issued May 14, 1991 to Holton describes such a synthesis.

Despite the advances made in the semi-synthesis of the paclitaxel molecule in the above described processes, there remains a need for more efficient protocols for the synthesis of paclitaxel in order to increase efficiencies in yields and production rates. There remains such a need for semi-synthesis that may be implemented into commercial processes. There is a further need for efficient protocols for the synthesis of paclitaxel analogs, intermediates and various A-ring side chain structures.

SUMMARY OF THE INVENTION

It is an object of the present invention to provide a new, useful and efficient protocol for the attachment of a protected A-ring side chain paclitaxel precursor to a protected baccatin III skeleton which may then be converted into paclitaxel.

Another object of the present invention is to provide methods of production of various precursor compounds including a paclitaxel-analog A-ring side chain that can be condensed with a protected baccatin III backbone which, after a combination of acylation and deprotections, yields paclitaxel.

Still a further object of the present invention is to provide an efficient and cost effective protocol for the semi-synthesis of paclitaxel.

According to the present invention, an N-CBZ protected C-2' benzyl protected (2R,3S)-3-phenyl isoserine A-ring side chain is coupled to a C-7 TES protected baccatin III backbone, after which the coupled condensation product undergoes a variety of deprotections and acylation to form paclitaxel. According to the present invention, a process of producing paclitaxel from an intermediate having the general formula:

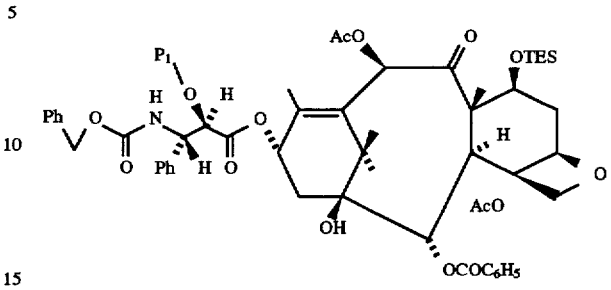

wherein $P_1$ is a hydrogenatable benzyl protecting group comprises the steps of deprotecting and acylating the intermediate compound at the nitrogen position of the A-ring side chain to replace the CBZ protecting group with PhCO. Next, the process includes deprotecting the C-7 TES baccatin III backbone at C-7 to replace the TES protecting group with hydrogen and deprotecting the side chain at the C-2' position to replace $P_1$ with hydrogen. This process includes the step of condensing the N-CBZ protected C-2' benzyl protected (2R,3S)-3-phenyl isoserine side chain with the C-7 TES protected baccatin III taxane to produce the intermediate and thereafter conducting the deprotections and acylation.

Preferably, the deprotection at the C-7 site to remove the TES protecting group occurs before the removal of the hydrogenatable C-2' benzyl protecting group. Here, the step of deprotecting and acylating the side chain nitrogen occurs before the step of deprotecting at C-7 to remove the TES protecting group. Alternatively, the deprotecting at the C-7 site occurs before the step of deprotecting and acylating in the side chain nitrogen. The step of deprotecting to remove the TES protecting group at C-7 is preferably accomplished in acetonitrile in the presence of and hydrofluoric acid.

According to one process described herein, the step of deprotecting and acylating the side chain at the nitrogen site is accomplished by dissolving the intermediate compound in isopropanol and thereafter mixing with Pearlman's catalyst under a hydrogen atmosphere to form a first mixture and thereafter reducing the first mixture to residue, taking up the residue in a solvent and a tertiary amine base to which benzoyl chloride is thereafter added. Here the solvent is selected from a group consisting of ethyl acetate and toluene and the tertiary amine base is preferably triethylamine.

These and other objects of the present invention will become more readily appreciated and understood from a consideration of the following detailed description of the exemplary embodiments.

DETAILED DESCRIPTION OF THE EXEMPLARY EMBODIMENTS

The present disclosure is broadly directed to a chemical process for the efficient production of paclitaxel, intermediates and precursors therefor. More specifically the present invention concerns the semi-synthesis of paclitaxel by esterifying (suitably protected) 3-phenylisoserine acids having hydrogenatable benzyl protecting groups at C-2' to the C-13 hydroxyl of 7-O-protected baccatin III. More particularly, the present invention utilizes triethylsilyl (TES) protection at the C-7 site. The general process described herein involves the production of C-7 TES baccatin III, the production of the suitably protected 3-phenylisoserine acid having a hydrogenatable benzyl protecting group at C-2', the condensation of the two compounds, and the subsequent deprotection and acylation of the condensation product to form paclitaxel.

A. Production of C-7 TES Protected Baccatin III

As a starting point in the semi-synthesis of paclitaxel according to the exemplary embodiment of the present invention, it is necessary to provide the baccatin III backbone onto which the paclitaxel-analog side chain may be attached. According to the present invention, it is preferred that this backbone be in the form of the basic baccatin III backbone that is protected at the C-7 site with a TES protecting group. Particularly, it is desired to provide a reaction intermediate of the formula:

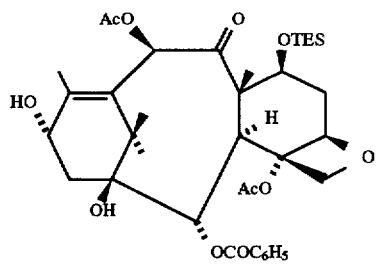

Formula 5

The compound of formula 5 may hereinafter be referred as TES-protected baccatin III, and its preparation may be accomplished by the various routes described in the literature.

One such route is described in Denis et al, "A highly Efficient, Practical Approach to Natural Taxol, *Journal of the American Chemical Society*, p. 5917 (1988). Here, 10-deacetylbaccatin III is first converted to C-7 TES protected 10-deacetylbaccatin III and subsequently the C-7 TES protected 10-deacetylbaccatin III is converted to C-7 TES protected baccatin III by the acylation of the compound at the C-10 location. C-7 TES protected 10-deacetylbaccatin III is achieved according to the following reaction:

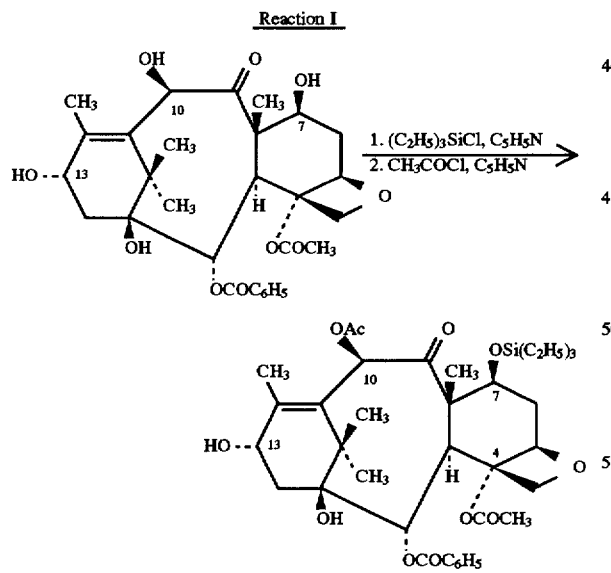

Here, 10-deacetylbaccatin III is reacted with a large excess of TES-Cl and pyridine to produce C-7 TES protected 10-deacetylbaccatin III. The product is next acylated utilizing an excess of acetyl chloride and pyridine to produce C-7 TES baccatin III.

Alternatively, C-7 TES protected baccatin III may be efficiently produced according to the procedure described in Kant et al "A Chemo Selective Approach To Functionalize the C-10 Position of 10-deacetylbaccatin III Synthesis and Biological Properties of Novel C-10 Taxol® Analogs", *Tetrahedron Letters*, Vol. 35, No. 31, TP5543–5546 (1994). As described in this article, C-7 TES protected C-10 hydroxy baccatin III may be obtained according to the reaction:

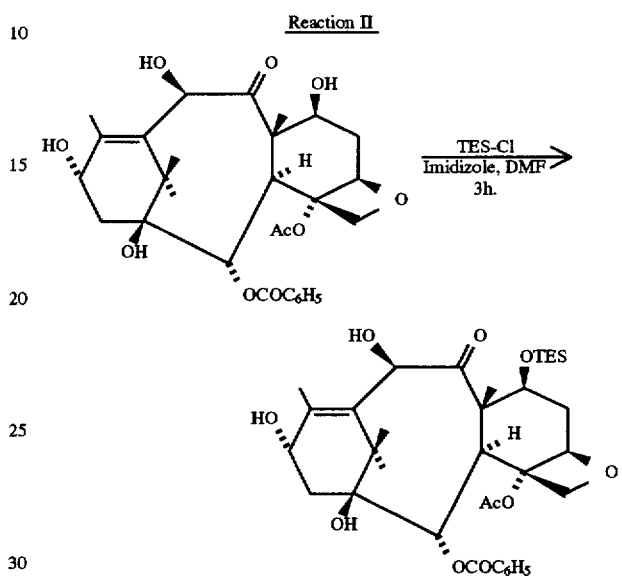

Here, imidazole is added while stirring to a solution of 10-deacetylbaccatin III in dimethylformamide (DMF) under a nitrogen atmosphere. Triethylsilyl chloride (TES-Cl) is then added dropwise over a period of approximately five minutes. The resulting solution is stirred or otherwise moderately agitated for three hours after which the mixture is quenched with water and extracted with two portions of either diethyl ether or methyl t-butyl ether, and the combined organics are mixed and washed with four portions of water and one portion brine. The organic and aqueous layers are then separated and the organic layer is dried and reduced under vacuum to form a crude solid. This crude solid is then recrystallized from ethyl acetate/hexane to produce C-10 hydroxy C-7 TES baccatin III.

Next, the C-10 hydroxy C-7 TES baccatin III is acylated to produce C-7 TES baccatin III according to the following reaction:

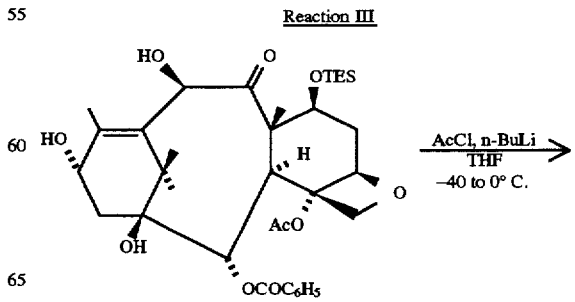

-continued
Reaction III

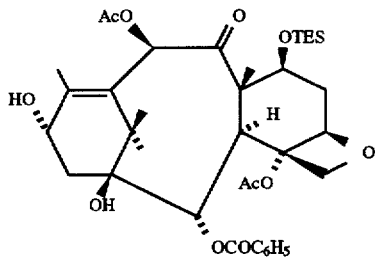

The C-10 hydroxy C-7 TES baccatin III is dissolved-in anhydrous tetrahydrofuran (THF) and the solution is cooled under a nitrogen atmosphere to a temperature of less than −20° C. n-Butyl lithium (1.6M in hexane) is added dropwise, and the mixture is stirred at the reduced temperature for approximately five minutes. Acetyl chloride is then added dropwise and the mixture warmed to 0° C. over an interval of five minutes and then stirred at that temperature for approximately one hour. The mixture is then quenched with water and reduced under vacuum, after which the residue is taken up in ethyl acetate and washed once with water and then brine. The organic layer may then be dried and reduced under vacuum, and the residue recrystallized with ethyl acetate/hexane to yield C-7 TES baccatin III as a white solid. The selected electrophile is AcCl. A yield of 90% was reported in this article.

Alternatively, of course, the C-7 TES protected baccatin III can be made directly from baccatin III instead of the route described above for the conversion from 10-deacetylbaccatin III.

B. Production of N-carbamate Protected C-2' hydroxyl-Benzyl Protected (2R,3S) 3-Phenyl Isoserine A-ring Side Chain The second precursor necessary for the semi-synthesis of paclitaxel according to the present invention is the N-carbamate protected C-2' hydroxyl-benzyl protected (2R, 3S) phenyl isoserine side chain having the general formula:

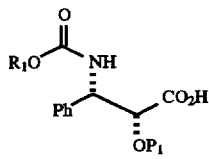

Formula 6 wherein $R_1$ is an alkyl, olefinic, or aromatic $PhCH_2$ and $P_1$ is a hydrogenatable benzyl protecting group The preferred hydrogenatable benzyl protecting group is a benzyloxymethyl (BOM) protecting group although other hydrogenatable benzyl protecting groups, including benzyl, are believed suitable as well. The preferred N-carbamate protecting group is benzyloxycarbonyl (CBZ). The starting compound to produce the desired side chain is (2R,3S)-3-phenylisoserine ethyl ester to produce N—CBZ protected (2R,3S)-3-phenylisoserine ethyl ester according to the reaction:

Reaction IV

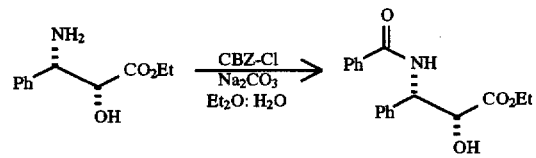

Here, (2R,3S)-3-phenylisoserine ethyl ester was alternatively dissolved in either equal parts diethyl ether:water or equal parts methyl t-butyl ether:water and the solution was cooled to 0° C. The sodium carbonate was then added to the solution and benzylchloroformate was added dropwise over an interval of about five minutes and the resulting mixture stirred at 0° C. for approximately one hour. After the one hour stirring, the solution was then poured into water and extracted with methylene chloride or ethyl acetate, as desired. The organic layer is separated, dried and reduced under vacuum to residue. The residue was then recrystallized from ethyl acetate:hexane to result in N—CBZ protected (2R,3S)-3-phenylisoserine ethyl ester having the formula:

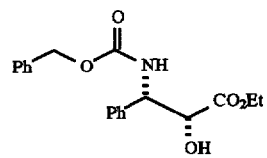

Formula 7

The N—CBZ protected (2R,3S)-3-phenylisoserine ethyl ester was next protected by the hydrogenatable benzyl protecting group, in several ways. For example, one route to the desired hydrogenatable benzyl protected side chain is as follows:

Reaction V

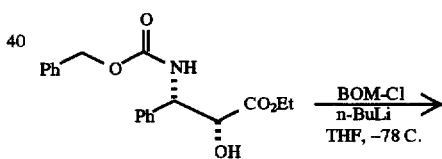

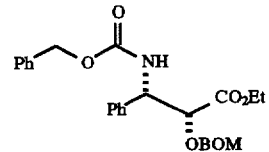

Here, the CBZ protected (2R,3S)-3-phenylisoserine ethyl ester is dissolved in anhydrous THF under a nitrogen atmosphere and cooled to a reduced temperature such as −40° C. or −78° C., for example, in a dry ice/acetone bath followed by the dropwise addition of an alkylithium agent, such as n-butyl lithium, although it is desirable that the alkylithium agent be a straight chain alkyl. In any event, the reaction is best done at a temperature no greater than 0° C. The resulting mixture was stirred for about ten minutes. Benzyloxymethyl chloride (BOM—Cl) was then added dropwise over an interval of about five minutes and the mixture stirred for approximately two to five hours at the reduced temperature. Thereafter, the solution was warmed to −0° C. and quenched with water. The resulting mixture is reduced under vacuum to residue, and this residue is thereafter taken up in ethyl acetate and washed with water and brine. The organic layer may then be dried and reduced under vacuum and the residue recrystallized from ethyl acetate:hexane or chromotographed with ethyl acetate:hexane to give the compound:

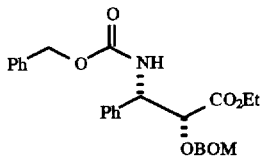

Formula 8

Another route in the production of the compound according to formula 8 is accomplished by dissolving the compound N—CBZ (2R,3S)-3-phenylisoserine ethyl ester in anhydrous methylene chloride. Thereafter, a tertiary amine base, such as diisopropylethylamine, is added along with BOM-Cl and the mix is refluxed for twenty-four hours. While this reaction route will produce N—CBZ protected C-2' [hydroxyl] protected (2R,3S)-3-phenylisoserine ethyl ester, the reaction proceeds much slower than the preferred route, discussed above.

In either instance, the resulting protected (2R,3S)-3-phenylisoserine ethyl ester compound of formula 8 may simply be converted to the N—CBZ protected C-2' O-BOM-protected (2R,3S) phenylisoserine intermediate hydroxyl by the reaction:

Reaction VI

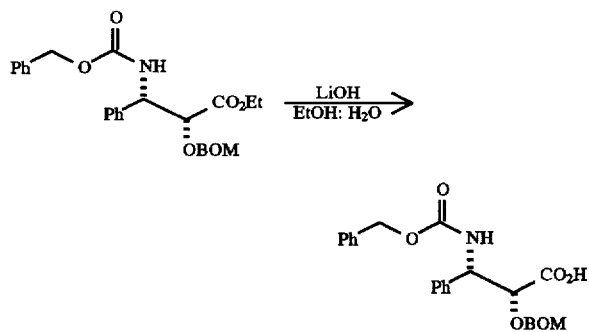

Here, the protected (2R,3S)-3-phenylisoserine ethyl ester is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1N HCl) and extracted with ethyl acetate. The resulting organic layer is separated, dried and reduced under vacuum. The residue acid is then isolated for use without further purification. This produces the desired side chain having the general formula:

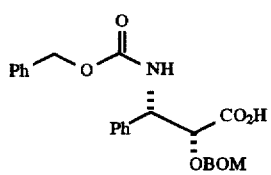

Formula 9

Benzyl itself is another example of a hydrogenatable benzyl protecting group that may be used instead of BOM. The compound of the formula:

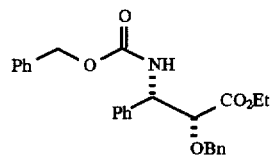

Formula 10 was therefore produced as above with the substitution of benzyl bromide for BOM-Cl in Reaction V according to the reaction Reaction VII

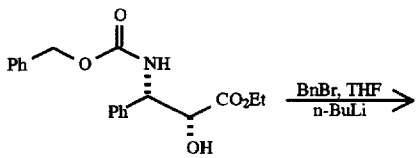

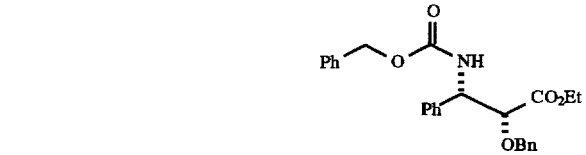

Here, the CBZ protected (2R,3S)-3-phenylisoserine ethyl ester is dissolved in anhydrous THF under a nitrogen atmosphere and cooled to a reduced temperature such as –40° C. or –78° C., for example, in a dry ice/acetone bath followed by the dropwise addition of an alkyllithium agent, such as n-butyl lithium, although it is desirable that the alkyllithium agent be a straight chain alkyl. The resulting mixture was stirred for about ten minutes. Benzyl bromide (BnBr) was then added dropwise over an interval of about five minutes and the mixture stirred for approximately two to five hours at the reduced temperature. Thereafter, the solution was warmed to –0° C. and quenched with water. The resulting mixture is reduced under vacuum to residue, and this residue is thereafter taken up in ethyl acetate and washed with water and brine. The organic layer may then be dried and reduced under vacuum and the residue recrystallized from ethyl acetate:hexane or chromatographed with ethyl acetate:hexane to give the compound of Formula 10.

Alternatively, the compound of Formula 10 may be obtained according to the reaction:

Reaction VIII

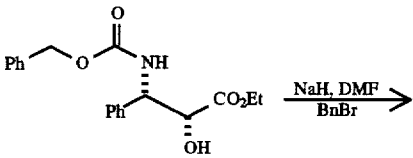

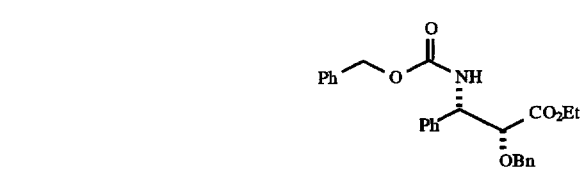

Here, to a stirred solution of NaH in anhydrous DMF under $N_2$ was added Formula 7 dissolved in DMF over five minutes. The mixture was then stirred at 0° C. for one half hour. After which time benzyl bromide (1.1 equivalents) was added dropwise over five minutes and the reaction stirred for two hours. The mixture was then quenched with $H_2O$. Thereafter, a selected one of diethylether and methyl t-butyl was added. The organic layer was then washed with four portions of $H_2O$, brine, and then dried and reduced under vacuum to produce Formula 10. Formula 10 may then be readily converted into:

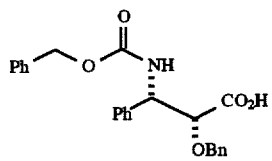

Formula 11 by the process of Reaction VI, above.

C. Condensation of C-7 TES Protected Baccatin III and the Side Chain

The side chain designated above as Formula 9 (or Formula 11) as well as the C-7 TES protected baccatin III may now be condensed, again by a variety of routes. By way of example, this condensation may proceed in the presence of a diisopropylcarbodiimide and dimethylamino pyridine (DMAP) in toluene at 80° C. according to the reaction:

The combined organics were then washed with hydrochloric acid (5%), water and, finally, brine. The organic phase was separated, dried and reduced under vacuum. The resulting residue was then dissolved in ethyl acetate:hexane and eluted over a silica gel plug. The eluent is then reduced under vacuum to result in the compound:

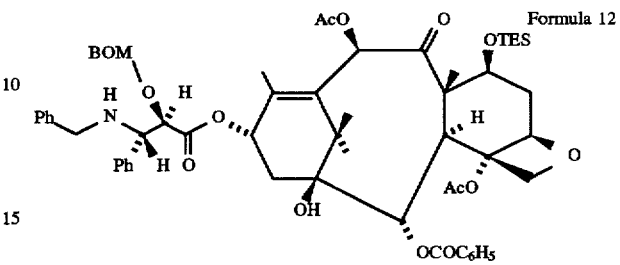

Formula 12

D. Deprotections and Acylation to Form Paclitaxel

The compound according to the Formula 12 may now be converted into paclitaxel by removing the CBZ protecting group and acylating the side chain, removing the TES protecting group and removing the hydrogenatable benzyl protecting group. Here, several convenient routes have been found although in general, it is necessary to deprotect the

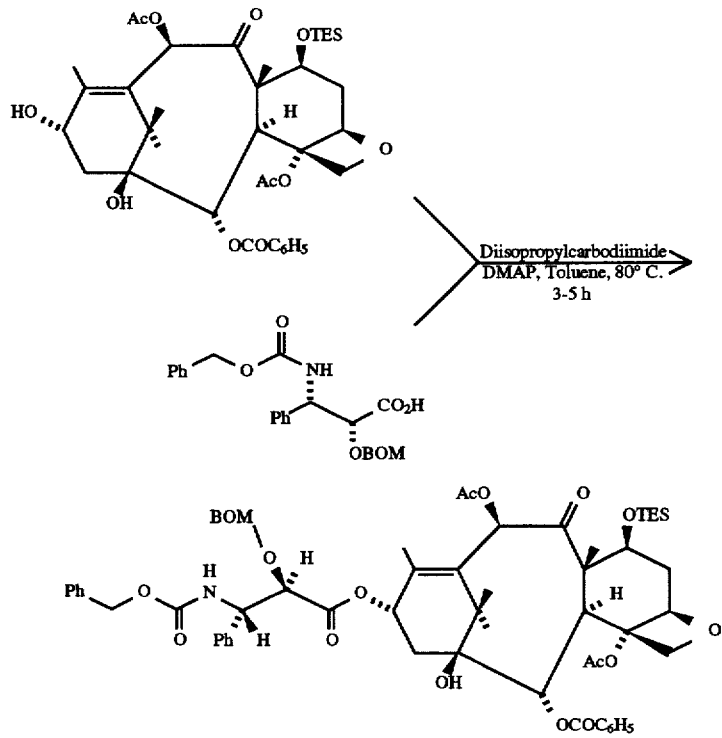

Here, C-7 TES protected baccatin III (1 equivalent) and the acid side chain of Formula 9 (6 equivalents) are dissolved in toluene. To this mixture DMAP (2 equivalents) and diisopropylcarbodiimide (6 equivalents) are added, and the resulting mixture heated at 80° C. for three to five hours. It should be noted, however, that other dialkyl carbodiimides may be substituted for the diisopropylcarbodiimide, with one example being dicyclohexylcarbodiimide (DCC). Next, the solution was cooled to 0° C. and held at this temperature for twenty-four hours. After this time it was filtered and the residue rinsed with either ethyl ether or methyl t-butyl ether.

C-7 site by removing the TES protecting group prior to deprotecting the C-2' site with the hydrogenatable benzyl protecting group. If the TES protecting group is not removed first, it is believed difficult at best to remove the hydrogenatable protecting group in a later processing step.

In any event, the preferred route of producing paclitaxel is to first remove the CBZ protecting group according to the reaction:

Reaction X

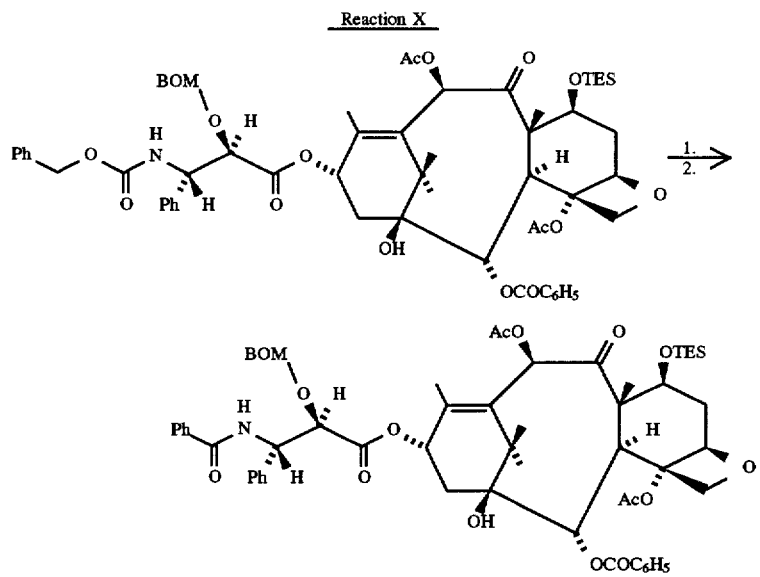

1. Pearlmans Cat. 1Atm, H₂tPrOH
2. Benzoyl Chloride, EtOaC, TEA

Here, the coupled product of Formula 12 is dissolved in isopropanol to which the Pearlman's catalyst is added. The resulting mixture is stirred under one atmosphere of hydrogen for twenty-four hours. Thereafter, the mixture is filtered through diatomaceous earth and reduced under vacuum to residue. The residue may then be taken up in ethyl acetate or toluene and a tertiary amine base, such as triethylamine is added. Benzoyl chloride was added dropwise, and the mixture stirred for two hours. The resulting mixture was then washed with dilute NaHCO₃, water, and finally brine. The resulting organic phase was then separated, dried and reduced under vacuum to yield the CBZ deprotected/acylated compound:

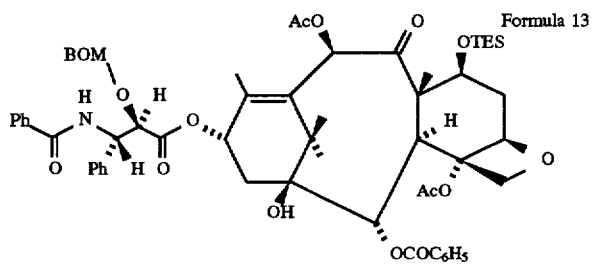

Next, the compound of Formula 13 is deprotected at C-7 according to the reaction:

Reaction XI

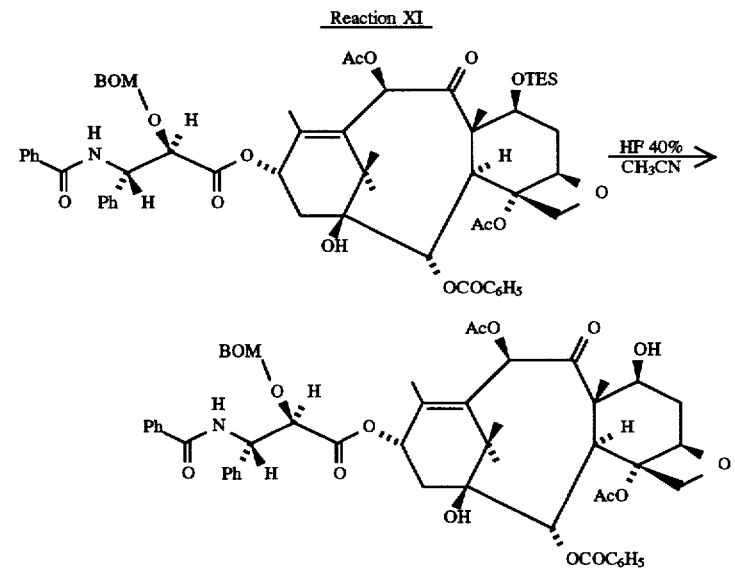

Here, the compound of Formula 13 was dissolved in acetonitrile (CH₃CN) at 0° C. Hydrofluoric acid (40% aqueous) was then added and the mixture stirred for ten hours while being held at 0° C. Thereafter, the mixture is diluted with ethyl acetate, saturated NaHCO$_3$, water and finally brine. The organic phase was separated, dried and reduced under vacuum to produce a deprotected product at the C-7 position according to the formula:

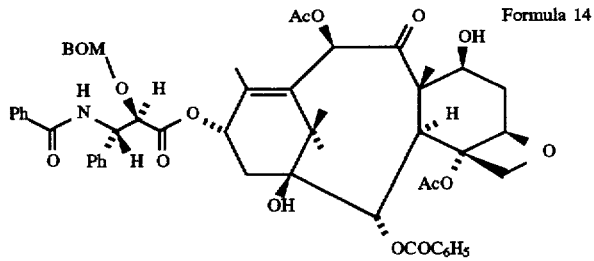

Formula 14

Finally, the compound of Formula 14 is deprotected at C-2' to remove the hydrogenatable benzyl (BOM) protecting group and to liberate the C-2' hydroxy group thereby resulting in the desired paclitaxel. This is accomplished according to the reaction:

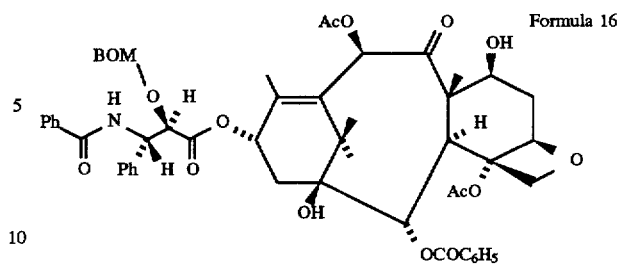

Formula 16

The compound of Formula 16 is dissolved in isopropyl alcohol and placed in a Parr bottle and Pearlman's catalyst was added. The mixture was hydrogenated for twenty-four hours at 40 psi of hydrogen. Thereafter, the mixture was filtered through diatomaceous earth and the eluent reduced under vacuum. The residue may then be column chromatographed according to any desired technique or recrystallized from ethyl acetate:hexane for the final paclitaxel product.

Accordingly, the present invention has been described with some degree of particularity directed to the exemplary

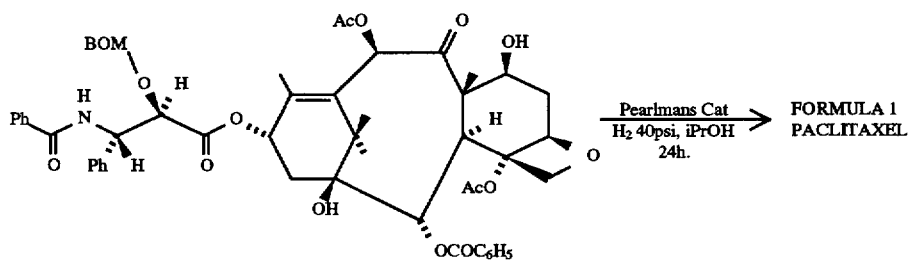

Reaction XII

Alternatively, the compound of Formula 12 may first be dissolved in CH$_3$CN at 0° C. and hydrofluoric acid (40% aqueous) added to deprotect the compound at the C-7 site by removing the TES protecting group. This results in a compound according to the formula:Z

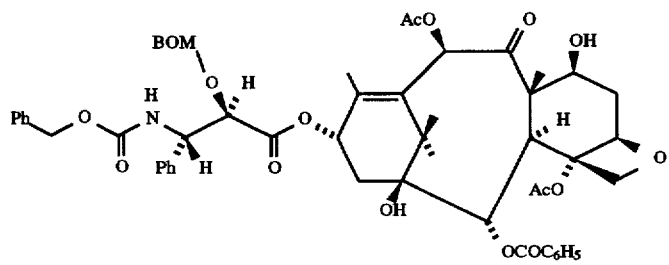

Formula 15

Next, the CBZ protecting group may be removed in a manner similar to that described above. Here, the compound of Formula 15 is dissolved in isopropanol and Pearlman's catalyst was added along with trifluoroacetic acid (TFA) (1 equivalent). The mixture was held at 40 psi of hydrogen at room temperature for approximately four days. This removes the CBZ protecting group and forms the C-2' BOM protected paclitaxel compound as a TFA salt. The mixture was filtered through diatomaceous earth and reduced under vacuum. Next, a base plus an acylating agent was added to the residue. Specifically, the TFA salt of the C-2' BOM protected compound was dissolved in pyridine and either benzoyl chloride or benzoic anhydride was added. The resulting product is:

embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A process of producing paclitaxel from an intermediate compound having the general formula:

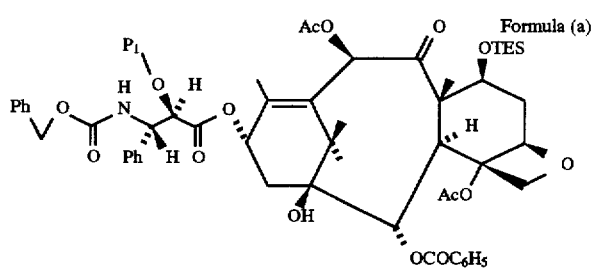

Formula (a)

wherein $P_1$ is a hydrogenatable benzyl protecting group comprising the steps of deprotecting and acylating the intermediate compound at the nitrogen position of the A-ring side chain to replace the CBZ protecting group with PhCO, deprotecting the side chain at the C-2' position to replace $P_1$ with H, and deprotecting at C-7 to replace the TES protecting group with H.

2. The process of claim 1 wherein the step of deprotecting at C-7 occurs before the removal of the hydrogenatable C-2' benzyl protecting group.

3. The process of claim 2 wherein the step of deprotecting and acylating the side chain nitrogen occurs before the step of deprotecting at C-7.

4. The process of claim 2 wherein the step of deprotecting at C-7 occurs before the step of deprotecting and acylating the side chain nitrogen.

5. The process of claim 1 wherein the step of deprotecting and acylating the side chain nitrogen is accomplished by dissolving the compound of Formula (a) in isopropanol and thereafter adding Pearlman's catalyst under a hydrogen atmosphere for a first interval of time to form a first mixture and thereafter reducing said first mixture to residue and taking up said residue in a solvent, adding a tertiary amine base and thereafter adding benzoyl chloride.

6. The process of claim 5 wherein said solvent is selected from a group consisting of ethyl acetate and toluene.

7. The process of claim 5 wherein the tertiary amine base is triethylamine.

8. The process of claim 1 wherein the step of deprotecting at C-7 is accomplished in acetonitrile in the presence of hydrofluoric acid.

* * * * *